United States Patent [19]

Duinker

[11] 4,168,435

[45] Sep. 18, 1979

[54] METHOD AND APPARATUS FOR TOMOGRAPHY WHEREIN SIGNAL PROFILES DERIVED FROM AN OUT-FANNING BEAM OF PENETRATING RADIATION CAN BE RECONSTRUCTED INTO SIGNAL PROFILES EACH CORRESPONDING WITH A BEAM OF PARALLEL INCIDENT RAYS

[75] Inventor: Simon Duinker, Bloemendaal, Netherlands

[73] Assignee: N.V. Optische Industrie "De Oude Delft", Netherlands

[21] Appl. No.: 814,989

[22] Filed: Jul. 12, 1977

[30] Foreign Application Priority Data

Jul. 19, 1976 [NL] Netherlands .................... 7607976

[51] Int. Cl.² .................. A61B 6/00; G01N 23/08
[52] U.S. Cl. ........................... 250/445 T; 364/414
[58] Field of Search .................. 250/445 T; 364/414

[56] References Cited

U.S. PATENT DOCUMENTS 3,983,398 9/1976 Boyd ............................ 250/445 T Primary Examiner—Alfred E. Smith
Assistant Examiner—T. N. Grigsby
Attorney, Agent, or Firm—O'Brien & Marks

[57] ABSTRACT

A method and apparatus for pre-processing by means of analogue techniques radiological information obtained by exposing a subject at various spaced positions on one side of this subject to an out-fanning, substantially flat beam of penetrating radiation. The resultant ray transmissions on the other side of the subject are recorded on a record medium as continuous and analogue signals located along a collection of recording paths each having a predetermined trajectory and a spatial orientation related to an associated position of exposure. The radiological information thus recorded is then scanned and read-out along another collection of adjacent scanning paths each having a predetermined trajectory which intersects different recording paths and likewise having a spatial orientation related to the associated position of exposure. The information thus read out represents analogue radiological information resulting from a virtual exposure to substantially parallel rays of penetrating radiation, and permits the reconstruction of desired laminal planes of the subject by means of a process involving a single convolution function.

15 Claims, 6 Drawing Figures

METHOD AND APPARATUS FOR TOMOGRAPHY WHEREIN SIGNAL PROFILES DERIVED FROM AN OUT-FANNING BEAM OF PENETRATING RADIATION CAN BE RECONSTRUCTED INTO SIGNAL PROFILES EACH CORRESPONDING WITH A BEAM OF PARALLEL INCIDENT RAYS

The invention relates to a method and apparatus for forming an image of a lamina of a subject under examination by means of penetrating radiation, such as X-rays, employing a source for producing a substantially flat, out-fanning beam of the penetrating radiation, a support for supporting the subject under examination so that this subject is irradiated by this beam, and a detector device for producing and processing signal profiles which are indicative of the radiation absorption in the lamina of the subject as determined by the beam and are the result of a relative movement between the subject and an assembly including the source of radiation and the detector device.

In the technique known as tomography it is possible to form a density image (tomogram) of a subject under examination that is representative of a "plan view" of a slice-like cross-section (lamina) of this subject. To this end, a relative movement is established between the subject and the assembly including the source of radiation and the detector device, and the subject under examination is irradiated from a series of positions, each position corresponding with a signal profile derived by the detector device. For example, the assembly is rotated about a vertical axis extending through the subject; alternatively, the assembly is stationary and the subject is rotated about this axis.

A tomogram can be reconstructed from a series of signal profiles thus derived by the detector device. It appears that in such a reconstruction the so-called point spread function degrades the definition or resolution of the tomogram. To eliminate this drawback, it has been proposed to preceed the superpositioning of signal profile information, as carried out during the processing of signal profiles provided by the detector device, by a pre-processing of these signal profiles such that the interfering point spread function is eliminated. In this procedure, each original signal profile is opto-electronically pre-processed to provide a new signal profile which, during the reproducing projection, provides a tomogram that is free from the interfering point spread function. It appears that, when use is made of a source of radiation irradiating the subject with a beam of parallel rays, one and the same point spread function applies to all points of the image field. However, the point spread function appears to be position-dependent when the irradiation is performed by means of an out-fanning beam. In other words, when a beam of parallel rays is used an exact correction with respect to the point spread function can be achieved as each original signal profile can be multiplied, fragment by fragment, by a given convolution integral. Such an exact correction and hence optimalization of the resolution cannot be achieved, however, when such a correcting operation is simply applied to a situation in which an out-fanning beam is employed.

For techno-economical reasons, it is unacceptable in the art of tomography to use a beam of parallel rays in a configuration in which the source of radiation is mounted at a relatively great distance from the subject under examination. One should rather contemplate a configuration in which a source for producing a substantially flat, out-fanning beam of radiation is mounted optimally close to the subject.

Computerized tomography systems are known which, by means of digital processing techniques, can transform digital data representative of radiation absorption signals obtained by out-fanning beams into signals representative of signal profiles obtained by beams of parallel rays. In such computerized tomography systems the detector device comprises a plurality of discrete detector elements. The output signals of these detector elements are subjected to an analogue-to-digital conversion and are stored in a digital memory system with information regarding the directions of the corresponding pencil beams of penetrating radiation. After all data obtained from one complete rotation of the object under examination relative to the apparatus is collected, a re-ordering process of this data is carried out to obtain signal profiles representative of fictitious beams of parallel rays. Back projection of these so-called parallellized profiles eventually yields a tomogram which is free from the blurring effects of a point-spread function. Such a computerized tomography system, however, cannot be applied to analogue tomography. This is because in analogue tomography it is essential that continuous and complete profiles be processed, so that any system wherein profile-elements corresponding to discrete detector elements are individually processed, is ruled out as a practical possibility. In order to be able, in analogue tomography, to apply the spatial filtering processes which are necessary to remove the effects of the point-spread function, it is necessary to find a method based on analogue electronic techniques, wherein from a collection of primary profiles resulting from out-fanning beams of radiation, another collection of profiles representative of fictitious beams of parallel rays is obtained. All these parallellized profiles can be subsequently subjected to the same spatial filtering process, since the back projection of parallel profiles gives rise to a point-spread function which is constant through out the plane.

It is an object of the invention to provide a solution to the problems outlined above, which solution by employing analogue processing techniques renders it possible to achieve an exact correction with respect to the point spread function throughout the entire optical field while using an out-fanning beam of radiation and applying a position-independent convolution function.

To achieve this object, the apparatus according to the invention is characterized by first means for recording in an analogue mode, in dependence upon a series of first positions successively taken by the source of radiation relative to the subject under examination, a collection of continuous primary signal profiles in analogue form corresponding therewith; and second means for scanning, in dependence upon a series of second positions related to said first positions, the collection of primary signal profiles in accordance with a collection of paths corresponding with this series of second positions, in such a manner that the signal profile fragments each corresponding with such a path together form a secondary signal profile that is presentative of the radiation absorption of the subject as a result of an imaginary beam of parallel rays incident from a direction corresponding with one of the first positions.

Due to its simple organization, an apparatus according to the invention can be manufactured at a relatively low cost price. Further advantages are, moreover, that relatively little space is required to accommodate the apparatus, and that, as parallel beams are reconstructed from out-fanning beams, the source of radiation can be mounted close to the subject, which permits efficient use of such a source of radiation and a low radiation dose while optimal resolution of the ultimate tomogram is achieved.

The invention will be described in greater detail hereinafter with reference to the accompanying drawings, in which.

Figure 1:
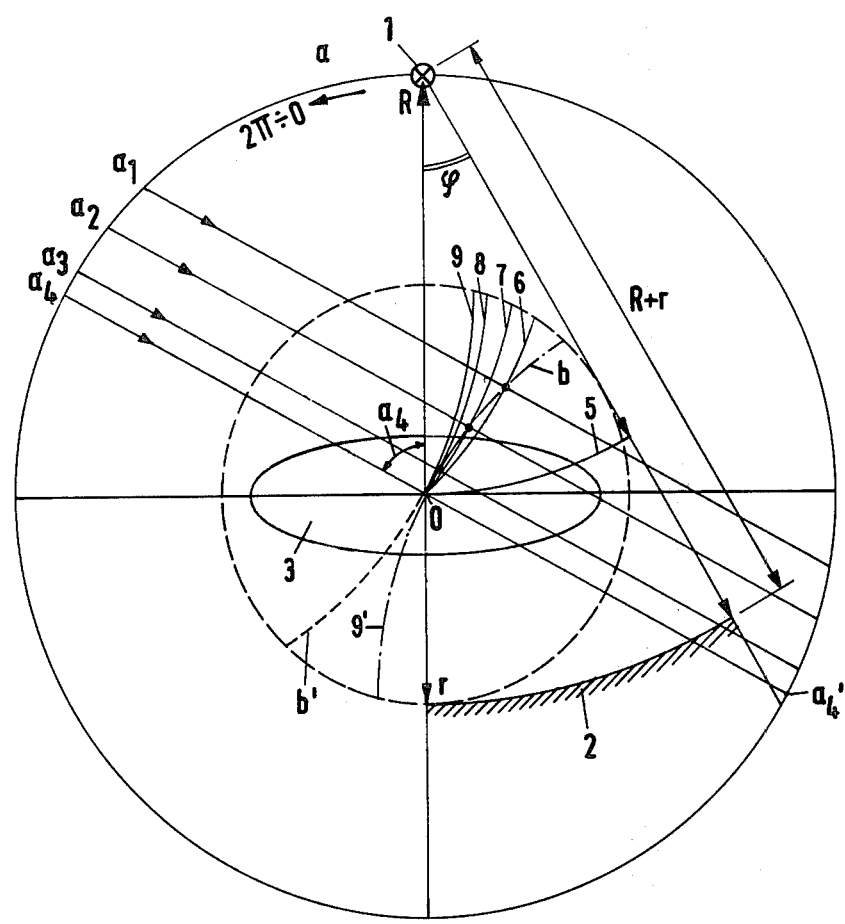
FIG. 1 shows a diagam with reference to which the principle of the present invention will be elucidated.

In the configuration shown in FIG. 1, a source for producing a substantially flat, out-fanning beam of penetrating radiation, such as X-rays, is designated by 1. A capture screen of a detector device is designated by 2. A subject 3 is placed between this capture screen and the source of radiation on a support (not shown). Without the invention being limited thereto, in the configuration shown in FIG. 1 it is assumed for simplicity that an assembly including the source of radiation and the detector device can perform a rotational movement about an axis O (normal to the plane of the drawing) extending through the subject, the source of radiation moving along a circular path having radius R. Self-evidently, it is also possible to fixedly mount the assembly and rotate the subject about the axis O. In both instances it is achieved that the subject can be irradiated from a series of positions on the circular path having radius R. The circular path having radius r is determined by the minimum distance required for an unobstructed rotation of the assembly, including collimators that may be necessary, about the subject under examination, or vice versa.

As will be explained later on, it is an advantage to bound the beam of radiation on one side by a flat plane defined by the axis of rotation extending through the centre of rotation O and the source of radiation itself. Such a boundary, which has been proposed in Dutch patent application No. 76,05687 too, has the advantages that the angular field of the capture screen as required for the detector device is considerably smaller than the angular field required in the event of an unbounded beam of radiation, and that the spreading of the radiation intensity is less due to the smaller beam width. To avoid image distortion at the edges of the capture screen, it is an advantage to give this screen an arcuate shape, the centre of curvature coinciding with the position of the source of radiation and the radius of curvature being R+r. It will be clear that when the capture screen is to concurrently receive a plurality of laminal images of the subject, this capture screen must have a spherical surface. When, in the configuration described above, the subject is irradiated by the out-fanning beam from the source of radiation, at a given position angle of the source-detector assembly relative to the subject a "transmission image" wil be projected on the capture screen, which image corresponds with a disc-shaped slice of the subject, the thickness of this slice being determined by the height of the flat beam of radiation and the "length" of the strip-like image being defined by the angular width (angle $\phi$) of the beam.

The detector device, which may be of a known per se type, preferably e.g. a detector device in the form of an X-ray image intensifier, is operative to convert a continuous radiation image in analogue form, e.g. an X-ray image, formed on the capture screen, which image is indicative of the radiation absorption in the respective lamina of the subject from the direction in question (position angle $\alpha$), to a corresponding, intensified electric image signal. After passing a thus-obtained electric image signal through a logarithmic intensifier, a signal is obtained that is representative of the density pattern associated with the lamina of the subject applying to the respective position angle $\alpha$. It will be clear that for a series of position angles $\alpha$, such as $\alpha_1$, $\alpha_2$, $\alpha_3$, $\alpha_4$ etc., a corresponding series of such electric signals can be achieved. After passing through the entire circle having radius R, a group of electric signals is obtained from which an image can be reconstructed that represents the complete density variation within the respective lamina of the subject, provided the angular width (angle $\phi$) of the beam is selected so that each element of the lamina of the subject under examination is irradiated from each position angle $\alpha$. It is observed in this connection that the electric signals (signal profiles) produced by the detector device are the result of using an out-fanning beam of radiation. This means that when during the further processing of such signal profiles it is tried to eliminate the point spread function, no exact correction is possible for the full image field, which means a degradation of the ultimately achieved tomogram.

This drawback can be eliminated by recording the signal profiles provided by the detector device, prior to their further processing, in a separate memory device in a specific manner. Particularly, a signal profile corresponding with each position angle of the source of radiation relative to the subject under examination is recorded as a continuous analogue signal located in accordance with a predetermined path. In order to be able to clearly indicate the direct relationship between the manner of recording and the instantaneous position of the device, an example of such a path is shown in FIG. 1 by the path sections 5, 6, 7, 8 and 9, such a recorded signal profile n corresponding with each position angle $\alpha_n$ of the source of radiation. In the configuration shown in FIG. 1, these signal profiles are recorded in analogue form in accordance with arc-shaped paths having their centre of curvature on the circle having radius R, each of these recorded signal profiles beginning in centre O of this circle. Consequently, signal profile 6 corresponding with position angle $\alpha_1$ is achieved by describing a circular arc from centre of curvature $\alpha_1$ at radius R, which arc begins in centre O. Each of the other signal profiles are recorded in an identical manner, resulting in a bundle of recorded signal profiles beginning in centre O, so that a collection of vane-like primary signal profiles is obtained.

It appears possible to scan such a collection of recorded primary signal profiles in analogue form in accordance with another collection of paths, in such a manner that by such a scanning a collection of secondary signal profiles can be constructed, in which each of these secondary signal profiles can be taken as being obtained from an imaginary beam of parallel incident rays. This may be appreciated for the primary signal profiles 5–9 shown in FIG. 1 by a closer consideration of this FIG. 1. To this end, this Figure shows a beam of parallel incident rays corresponding with the position angle $\alpha_4$, the primary signal profile fragments corresponding with these parallel incident rays being drawn as the points of intersection of the respective ray and the associated primary signal profile. In other words, the points of intersection between the ray originating from $\alpha_1$ and signal profile 6, the ray originating from $\alpha_2$ and signal profile 7, the ray originating from $\alpha_3$ and signal profile 8 and the ray originating from $\alpha_4$ and signal profile 9. It appears that the thus-obtained points of intersection lie on an arc-shaped path b going through the centre 0 and having a radius of curvature R and a centre of curvature $\alpha'_4$ that is diametrically opposite point $\alpha_4$ to define a diameter line that is determinative of the direction of incidence of the respective beam of parallel rays, in other words the centre of curvature $\alpha'_4$ is defined by $\alpha_4 + \pi$. Consequently, the secondary signal profile corresponding with such an arcuate scanning may be regarded as a signal profile derived from a beam of parallel rays. Therefore, each position angle $\alpha_i$ corresponds with a position angle $\alpha'_i$ related thereto and determinative of the arcuate scanning from which a secondary signal profile corresponding with an imaginary beam of parallel rays incident at the angle $\alpha_i$ can be reconstructed. In other words, by such a scanning it is possible to reconstruct from the collection of primary signal profiles the collection of secondary signal profiles, which secondary signal profiles can readily be subjected to a standardized exact correction with respect to the point spread function.

Such scannings should lag the recording of the primary signal profiles by a given angle, e.g. 30°, as all the primary signal profiles to be scanned must have been actually recorded. After scanning the respective group of primary signal profiles, this group may be erased and different information may be recorded in the erased portion of the record medium.

In principle, it is also possible to use a beam of radiation having an angular width twice that shown in FIG. 1. In such a situation, the second half of each primary signal profile should be recorded as schematically indicated by the chain-dotted arc 9, which is possible as the subject under examination is radiation-isotropic, which means that the absorption of the subject along a line depends only on the direction of this line and not on its sense. Self-evidently, in this situation the assembly including the source of radiation and the detector device need only rotate through an angle of $\pi$ radians relative to the subject in order to develop a complete tomogram. The reconstruction of the primary signal profiles thus-recorded by means of a beam of double angular width can be obtained either by scanning through $2\pi$ radians in accordance with "half" arcs b, or by scanning through $\pi$ radians along S-shaped paths, in other words in accordance with mirror-symmetrical arcuate paths b, b'.

The recording of the "half" primary signal profiles in the form of circular arcs going through the origin 0, as discussed with reference to FIG. 1, has the drawback that around this origin the lines of the patern are difficult to separate, as a result whereof and depending on the manner of scanning to obtain the secondary signal profiles, inaccuracies may occur around this origin. In fact, in the reconstruction of secondary signal profiles corresponding with beams of parallel rays, as discussed above, the scanning is performed practically tangentially to the respective primary signal profiles especially in the vicinity of this origin 0, which may lead to an unacceptably high inaccuracy.

Figure 2:
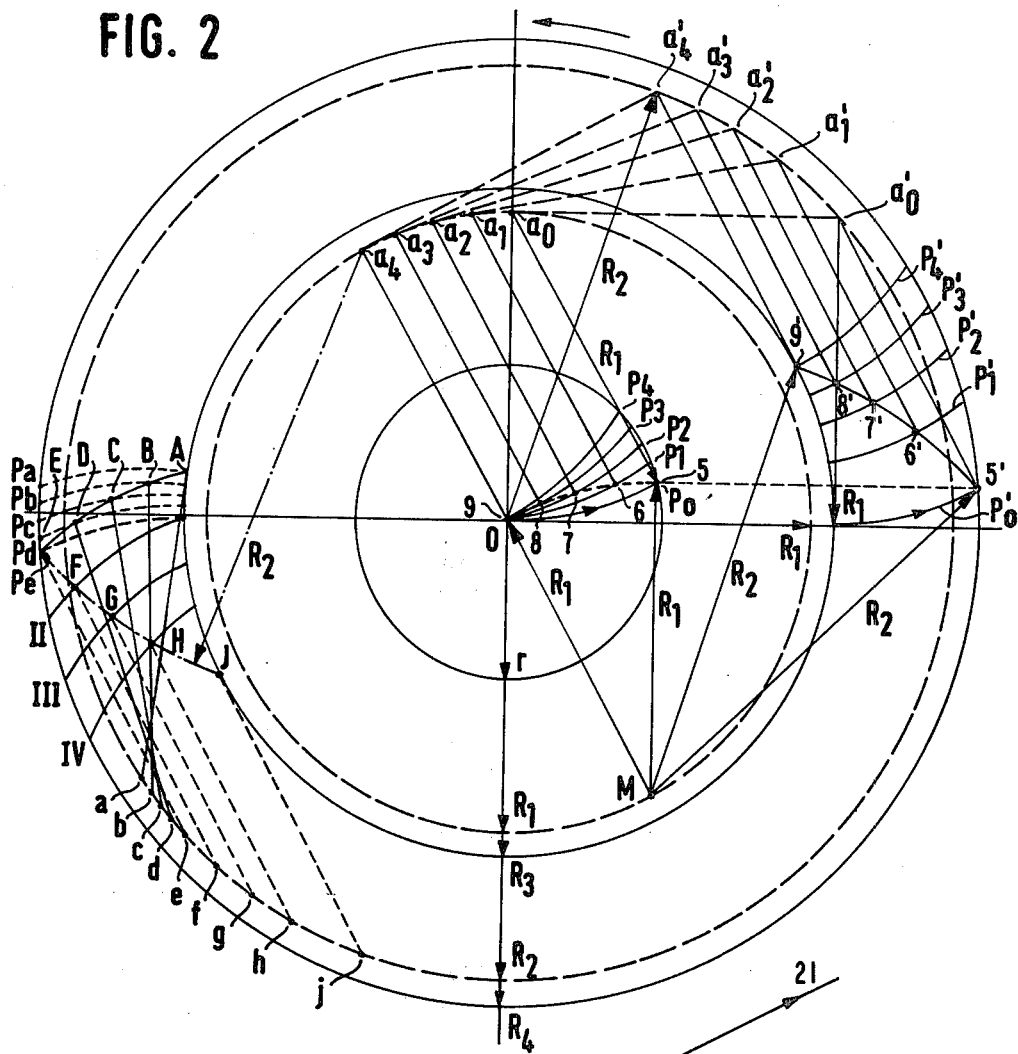
FIG. 2 shows a diagram illustrating a configuration lacking a drawback inherent in the configuration shown in FIG. 1.

To eliminate these drawbacks, consequently it is preferred to draw the primary signal profiles, instead of as vanes originating from the origin O as shown in FIG. 1, as arcuate spokes originating from a rim as schematically shown in FIG. 2. In this FIG. 2, the circle having radius $R_1$ is the path corresponding with a relative movement of the source of radiation with respect to the centre of rotation 0. Just as in FIG. 1, the circle having radius r in FIG. 2 is determined by the minimum distance required for an unobstructed rotation about the subject. The distance $R_3$ is the distance through which each time a position angle point $\alpha_1$ is shifted along the tangent to the circle $R_1$ in that point to come to the position angle point $\alpha'_i$ on the circle $R_2$ determinative of the respective primary "half" signal profile $p'_i$, which is recorded as an arc-shaped spoke from a rim having radius $R_3$.

Thus in a manner similar to that employed in the configuration shown in FIG. 1, by means of a series of position angle points, such as $\alpha'_0-\alpha'_4$, a collection of associated primary "half" signal profiles, such as $p'_0-p'_4$, is recorded. Without limiting the scope of invention, the distance $R_3$ is selected so that the locus of the extremities of the primary "half" signal profiles, which originally were on the circle having radius r, are now on a circle having radius $R_4$. In other words, point o of the original primary signal profile $p_o$ becomes the point 5' of the primary signal profile $P'_o$ etc. In FIG. 2, the circle having radius $R_2$ indicates the path of the source points shifted along the tangents through the distance $R_3$. This radius $R_2$ is defined by $R_2 = \sqrt{R_1^2 + R_3^2}$. In the case of a recording as achieved by means of a configuration as shown in FIG. 2, it appears that the reconstruction of the secondary "half" signal profiles corresponding with beams of parallel incident rays can be obtained by means of arc-shaped scanning paths having radius of curvature $R_2$ and each time described from the same centre of curvature M corresponding with the point of intersection of the circle about the point of rotation 0 and having the radius $R_1$ on the one hand and the ray of the parallel beam going through this point 0 on the other hand. In such a configuration, the points of intersection between the primary signal profiles and the scanning paths for achieving the secondary signal profiles are defined in a better manner. This is schematically shown in FIG. 2 for the position angle point $\alpha_4 + \pi$ and the circular arc determined thereby, which has a radius of curvature $R_2$. The respective points of intersection are indicated by 5', 6', 7', 8' and 9'. These points correspond with a beam of parallel rays incident at an angle $\alpha_4$. It will be clear from the above that as $R_3$ approaches 0, the configuration discussed with reference to FIG. 2 changes to the one discussed with reference to FIG. 1, Consequently, self-evidently the arrangement can be made so that each time two "half" profiles are concurrently recorded, as a result whereof a rotation of only $\pi$ radians is required.

Also in the configuration shown in FIG. 2 the scanning operation is delayed with respect to the recording of the primary signal profiles. The surface area within circle $R_3$ is not initially used for recording in the configuration shown in FIG. 2. If the thickness of the annular surface area situated between the circles having radii $R_1$ and $R_3$ can be selected sufficiently small, in which connection the resolution of the selected record medium forms the limit, the collections of primary signal profiles can be recorded in concentric annular areas within one another for a plurality of simultaneous tomograms. It can readily be seen (see in this respect the left-hand part of FIG. 2) that if, instead of drawing the collection of primary signal profiles for a series of discrete position angle values $\alpha_i$, these primary profiles are continuously drawn upon a continuous, preferably uniform, relative rotation of the source about the subject, as will be preferred in practice, the path of the primary profiles drawn will not be determined by circular arcs (Pa, Pb, . . ., Pe) but by involutes (A, B, . . ., E). It can further readily be seen that, nevertheless, by the described scanning in accordance with arc-shaped paths (J, H, . . ., E), again the secondary profile associated with a parallel beam is obtained.

In principle, the invention is not limited to the embodiments adapted to the configurations shown in FIGS. 1 and 2; the general principle of the invention, in which a collection continuous of primary signal profiles as derived by means of a substantially flat, out-fanning beam of radiation is recorded in analogue form in accordance with a given path pattern and a thus-recorded collection is subsequently scanned in accordance with another collection of scanning paths having a pattern so that the secondary signal profiles developed from this scanning may be regarded as to be derived by means of a beam of parallel rays, may be illustrated by the basic configuration shown in FIG. 6, in which various variants of the invention may be realized by an appropriate choice of the control functions determining the recording and scanning. In the configuration shown in FIGS. 1 and 2, these control functions are such that the recording of the primary signal profiles is performed in accordance with arc-shaped paths (discontinuous rotation) or in accordance with convolutes such as e.g. hypercycloids (continuous rotation), while the scanning thereof to form the secondary signal profiles is performed in accordance with arc-shaped paths. In general, these control functions may be selected so that both the primary signal profiles and the paths along which these profiles are scanned to produce the secondary signal profiles, form a simple line pattern. For example, there are the following possibilities: the primary signal profiles are recorded in analogue form in accordance with essentially linear paths either in juxtaposed or in superposed relationship, while the scanning is performed in accordance with arcuate paths intersecting the pattern of primary signal profiles; the primary signal profiles are recorded in analogue form in accordance with similar, juxtaposed or superimposed arcuate paths, while the scanning for the reconstruction of the secondary signal profiles is performed along linear paths intersecting the pattern of primary signal profiles; and the primary signal profiles are recorded in analogue form in accordance with essentially linear paths either in juxtaposed or in superimposed relationship, while the scanning is performed in accordance with essentially linear paths intersecting the pattern of primary signal profiles.

Figure 3:
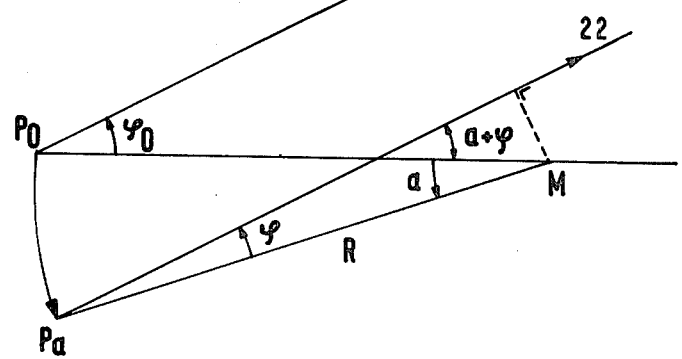
FIGS. 3, 4 and 5 show diagrams with reference to which the principle of the present invention will be discussed for a general instance.

In the situation in which the subject under examination and the assembly including the source of radiation and the detector device are rotated relative to each other, a series of primary signal profiles is obtained which each are a function of the position angle of the source of radiation. The relationship between the primary and secondary signal profiles for this situation will be derived with reference to FIG. 3. In the configuration shown in FIG. 3 it is assumed that the source of radiation moves along an arc-shaped path having radius R about the centre of rotation M from the position $P_o$ to the position $P_\alpha$ etc. By 21 is indicated a ray from the source of radiation when the latter is in position $P_o$, this ray 21 enclosing an angle $\phi_o$ with the line $P_oM$. By 22 is indicated a ray parallel to ray 21 and emanating from the source of radiation when the latter is in the position $P_\alpha$, i.e. after a rotation about centre of rotation M through an angle $\alpha$. The condition that this ray 22 is parallel with the ray 21 is that the sum of the angle $\phi$ enclosed between ray 22 and line $P_\alpha M$ and the angle $\alpha$ is equal to $\phi_o$. In other words, the secondary signal profile associated with direction $\phi_o$ is obtained by measuring the transmission of the ray enclosing an angle $\phi = \phi_o - \alpha$ with the connecting line $P_\alpha M$ upon each angular rotation $\alpha$ of the source of radiation. The distance from this ray to the centre of rotation M is $R.\sin\phi = R.\sin(\phi_o - \alpha)$. The radiation transmission values as measured when an out-fanning beam of radiation is used, e.g. a beam of X-rays, may or may not be logarithmatized, and recorded, for example so that the primary signal profiles derived from this out-fanning beam as a function of the above angle $\phi$, sine $\phi$, tangent $\phi$, or in general $f(\phi)$, are parallel, straight lines, the spacing of which is proportional to the position angle $\alpha$ of the X-ray sourde. The secondary signal profile corresponding with direction $\phi_o$ can then be found as a line through point $\phi = 0$, $\alpha = \phi_o$, and is further characterized by $\alpha + \phi = \phi_o$.

Figure 4:
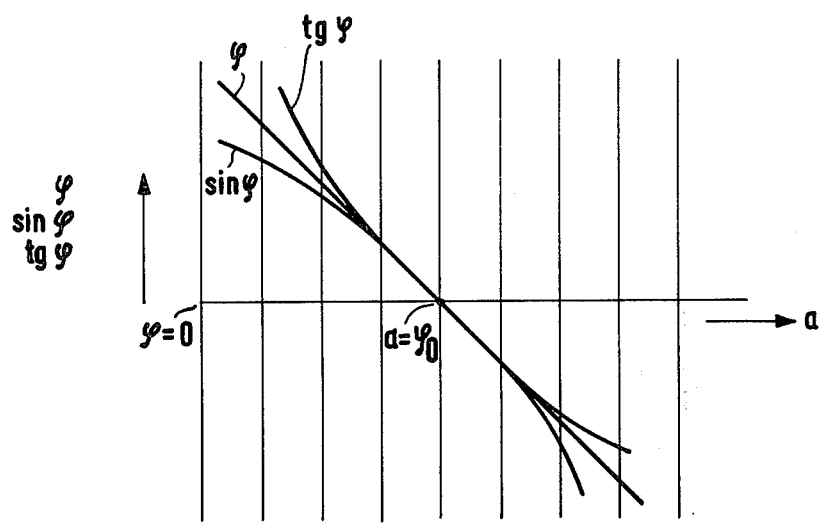

It will be clear that the path along which the scanning is performed for obtaining the secondary signal profile, is a straight line if the primary signal profile derived by measuring by means of an out-fanning beam is recorded as a function of the angle $\phi$, whereas this scanning path follows $f(\phi)$, if the primary signal profile is recorded as $f(\phi)$. This is illustrated in FIG. 4.

The secondary signal profiles should be available as a function of the irradiation angle $\phi$, particularly as a function of the distance $R.\sin\phi$ to the centre of rotation M, which implies that, if the scanning is performed in accordance with the right $\phi$ and, for example, the time is selected to be proportional to this distance, starting from $\phi = 0$, the scanning will have to be performed at increasing rate so as to maintain the first derivative with respect to time of the function $\sin\phi$ at a constant value.

The shape of the primary profile as obtained as a function of $\phi$ depends on the geometry of the source of radiation and the detector device, while this space can be affected further by the optic and optoelectronic distortions.

Figure 5:
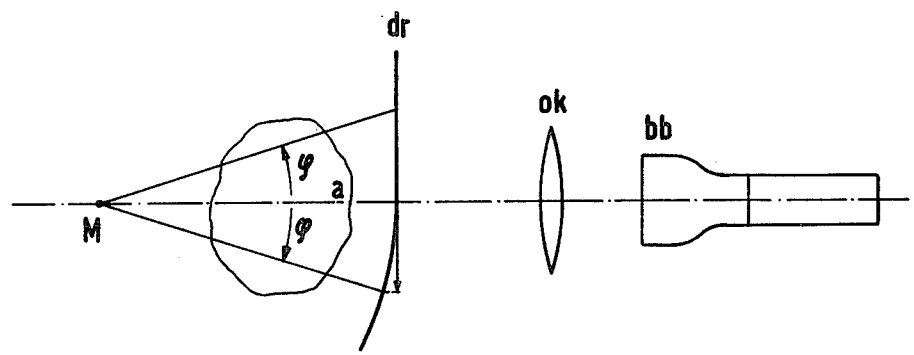

In fact, as appears from FIG. 5, in the event of a flat detector dr the primary profile follows tangent $\phi$, whereas in the event of a curved detector and the source of radiation disposed in a centra of curvature the primary profile follows sine $\phi$. The secondary profiles may, for example, be derived by an appropriate scanning in the image intensifier tube bb receiving the image developed by the detector device through a lens system ok.

In order to obtain an optimally uniform secondary profile, it may be advantageous to record the primary profiles so that the paths have such a width that they are contiguous. An optimalization with respect to the signal-to-noise ratio or the resolution can be obtained by varying the width of the path followed during the scanning of the primary profiles.

Figure 6:
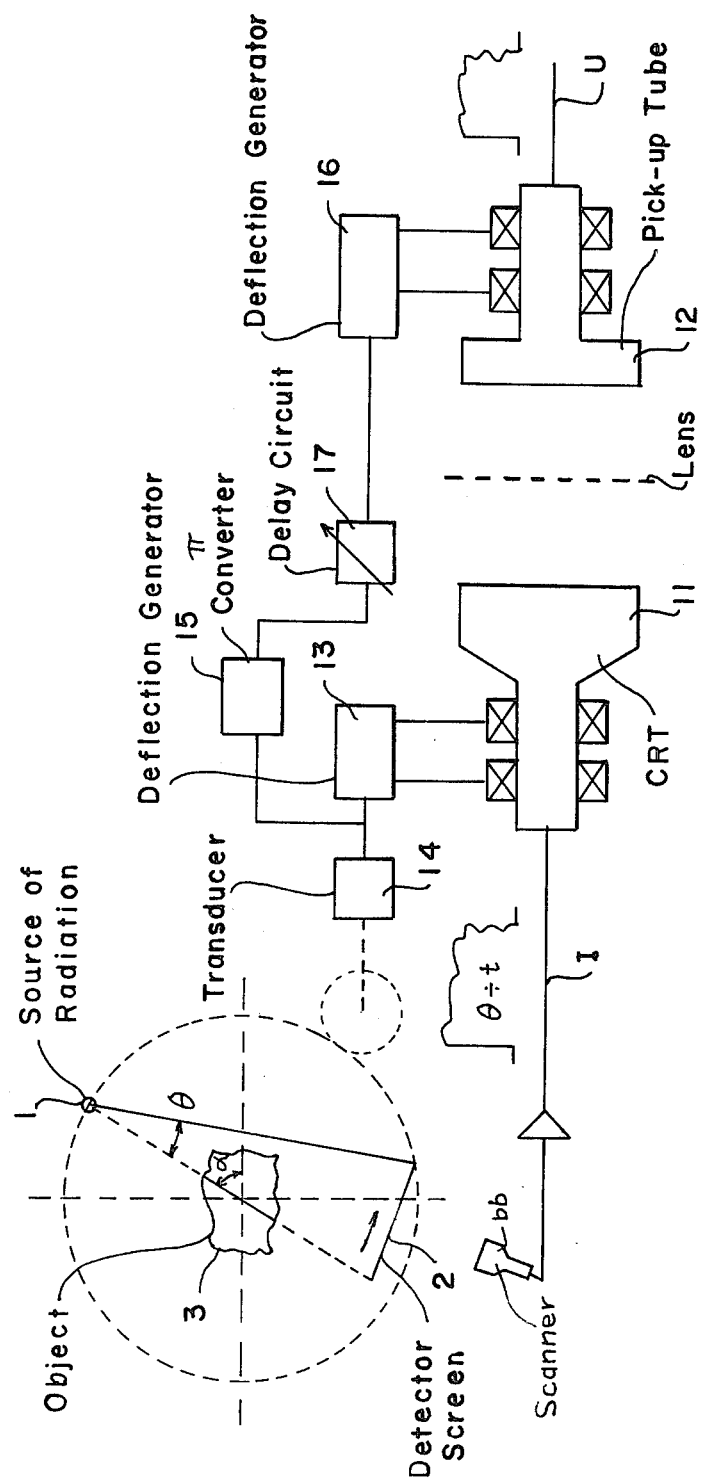
FIG. 6 shows a block diagram of an embodiment of the present invention.

In the block diagram of a general embodiment of the invention, as shown in FIG. 6, 11 is a cathode ray tube having a persistent phosphor screen on which the primary profiles, as presented by the electric signals from the scanning of the detector screen, can be recorded. Other recording devices, for example an electronic image converter tube or a continuous two dimensional magnetic sheet memory, may be used. The electric signals derived from the detector device are supplied to input I. A scanner such as TV pickup tube 12 is adapted to coact with the recording device to scan the information recorded in this device, the electric signals obtained as a result of the scanning being developed at output U. The paths along which the information supplied to input I is recorded are determined by a record control device such as a deflection generator 13. This record control depends on position information PI concerning the position or direction from which the subject under examination is irradiated by the source of radiation. In the configuration shown in FIG. 1, the series of positions from which the irradiation is performed is indicated by a circular path about the axis of rotation extending through the subject under examination. In this configuration the above position information consists of position angles such as $\alpha_1$, $\alpha_2$ etc. Assuming that the size of radius R is also known, the control information required for writing-in the primary signal profiles, which information is to be processed by the record control device 13, is thus complete. Consequently, in response to the position angle information supplied, which information is converted by translator or transducer 4 to corresponding position signals, the record control device 13 supplies control signals to the recording device 11, by means of which control signals the electric input signals supplied to recording device 11 are recorded, for example in accordance with the arc-shaped paths shown in FIG. 1. As stated earlier, by choosing different position information it can be achieved that, by means of the control signals for the recording device 11 as supplied by the record control device 13 as a result thereof, the patterns of recorded primary signal profiles are selectively modified. The position signals produced by translator 14 are supplied to a function converter 15, as a result whereof it is achieved that the control signals intended for the scan control device 16 are related in accordance with a given function to the signals by means whereof the control of device 13 is determined. In the configuration shown in FIG. 1, this relationship is represented by an angular difference $\pi$, so that each position angle $\alpha$ determinative of the control performed by device 13 is associated with a position angle $\alpha + \pi$ determinative of the control performed by device 16. By means of the control action exerted by this device 16 on the scanning device 12 it is achieved that the recorded primary signal profiles are scanned in accordance with the desired paths. In the configuration shown in FIG. 1, these paths are the arc-shaped paths each having a centre of curvature determined by $\alpha + \pi$ and a radius of curvature R. The control signals required for recording the primary signal profiles, as well as the control signals required for the scanning thereof, may be produced in a simple manner, for example, by means of electro-mechanical means serving for the transmission of angular information, which means are coupled to the drive mechanism producing the relative rotation of the subject relative to the assembly including the source of radiation and the detector device. The output signals obtained from such a scanning as developed at the output U of the scanning device are representative of the secondary signal profiles, which profiles may be regarded as signal profiles produced by the irradiation by means of an imaginary beam of parallel rays. As explained in the above, the scanning action performed by the scanning device 12 should lag a given period of time with respect to the recording of the primary signal profiles. To this end, a delay device 17 is connected between the function converter 5 and the scan control device 16. If desired, this delay device may be a variable one in order to permit selective adjustment of the delay and adaptation thereof to the conditions of operation.

Output signal U produced by the scanning device 12 is readily suited for further processing. As an exact correction with respect to the point spread function has been performed previously, a high resolution tomogram can readily be obtained therefrom by superposition, in spite of the fact that a source of radiation producing an out-fanning beam is used. Although, primarily, the practical realization of the present apparatus will involve tomographic image reconstruction in analog manner, of course it is readily possible to digitalize the output signals U and to perform the image reconstruction point-by point by means of a computer. The latter procedure may prove advantageous if not the entire cross-section but only specific parts thereof are considered of interest.

I claim:

1. A method of pre-processing radiolical information by means of electronic analogue techniques for use in a process for reconstructing an image of a desired lamina of a subject, said method comprising:

projecting substantially flat, out-fanning beams of penetrating radiation through the subject in the plane of the desired lamina at succeeding angular positions;

detecting the projected beams passed through the subject to produce a plurality of continuous electrical primary profile signals;

recording a plurality of juxtaposed continuous primary signal profiles from said primary profile signals to the subject on a record median along a plurality of recording paths each having a predetermined trajectory and spatial orientation related to the angular position during the projecting of the corresponding beam of penetrating radiation; and scanning and reading-out fragments of a plurality of series of adjacent primary signal profiles from the recorded profiles along a corresponding plurality of scanning paths each having a predetermined trajectory intersecting the corresponding series of the recording paths and also having a spatial orientation relating to the angular positions during the projecting of a corresponding series of the projected beams of penetrating radiation to generate a plurality of secondary profile signals each corresponding to parallel portions of the corresponding series of beams suitable for reconstructing the image of the selected lamina of the subject.

2. An apparatus for forming an image of a lamina of a subject under examination by means of penetrating radiaion comprising a source for producing a substantially flat, out-fanning beam of said penetrating radiation, a support for supporting the subject under examination so that said lamina of the subject is irradiated by said beam in the plane of the lamina, means for detecting the beam passing through the subject and for producing a continuous primary profile signal which is indicative of the radiation absorption in the lamina of the subject as determined by said beam, said support including means for producing relative movement between said subject and an assembly including said source of radiation and said detecting and primary profile signal producing means through a plurality of succeeding angular positions so that a plurality of the primary profile signals can be produced at the corresponding plurality of angular positions, first means for recording a plurality of continuous primary signal profiles corresponding with said plurality of primary profile signals and along a corresponding plurality of recording paths each having a trajectory and spatial relationship corresponding to the respective relative angular position of the subject and the assembly, and second means for scanning a plurality of series of the primary signal profiles along a plurality of scanning paths each having a trajectory intersecting the respective series of the recording paths and for producing a plurality of secondary profile signals each corresponding to parallel portions of a corresponding series of the plurality of beams projected by the source.

3. An apparatus according to claim 2, wherein said first means for recording said primary signal profiles includes record control means arranged so that each of said primary signal profiles is recorded in accordance with an arc-shaped path having a radius $R_1$, the center of which, in unique relationship with a respective one of said relative angular positions between the subject and the assembly is on a circle having radius $R_2$, in which $R_2 \geq R_1$, around a point 0 representing the axis of rotation of the source of radiation with respect to the subject, the beginning of each primary signal profile being on a circle around said point 0 having radius $R_3$, in which $R_3 \geq 0$ but may be $< R_2$; said beam produced by said source has one edge that coincides with the axis of rotation; and said second means for scanning the primary signal profiles includes scan control means arranged so that said plurality of primary, arc-shaped signal profiles are scanned in accordance with likewise arc-shaped paths each having a radius $R_2$ and a respective centre of curvature M which is in a point on said circle having radius $R_1$, the center of curvature M corresponding with an end of a diameter of the circle of radius $R_1$ indicating the direction of parallel beam portions corresponding to the respective series of primary signal profiles scanned.

4. An apparatus according to claim 2 including radiation bounding means for bounding the spreading of the out-fanning beam so that each primary signal profile has such a length corresponding to one half of the respective lamina of the subject, which one half is bounded by said axis of rotation and is completely irradiated.

5. An apparatus according to claim 3 wherein said record control means and said scan control means derive their control signals from electromechanical means for generating and transferring angle information about the relative movement of the subject with respect to the assembly of said source of radiation and said detecting and primary profile signal producing means.

6. An apparatus in accordance with claim 2 wherein said first means is adapted to record a plurality of pluralities of primary signal profiles that are located within concentric, annular areas; and said second means is adapted to scan said plurality of pluralities of primary signal profiles in accordance with a corresponding plurality of pluralities of scanning paths.

7. An apparatus according to claim 2 wherein said first means is adapted to record said primary signal profiles in accordance with essentially linear paths; and said second means is adapted to scan the pattern of primary signal profiles in accordance with arcuate paths intersecting said primary signal profiles.

8. An apparatus according to claim 2 wherein said first means is adapted to record said primary signal profiles in accordance with arcuate paths; and said second means is adapted to scan the pattern of primary signal profiles in accordance with essentially linear paths intersecting said primary signal profiles.

9. An apparatus according to claim 2 wherein said first means is adapted to record said primary signal profiles is accordance with linear paths; and said second means is adapted to scan the thus-recorded primary signal profiles in accordance with likewise linear, parallel paths intersecting the respective primary profiles at a fixed angle.

10. An apparatus according to claim 2 wherein said first means is adapted to record said primary signal profiles in accordance with paths that are longitudinally contiguous with one another; and said second means includes facilities for selectively adjusting the width of the paths along which the respective primary signal profiles are scanned.

11. An apparatus according to claim 2 including delay means for delaying the operation of said second means relative to that of said first means.

12. An apparatus according to claim 11 wherein said delay means includes setting means for setting the delay to be introduced at a selected value.

13. An apparatus according to claim 2 wherein said first and second means are united in a memory device in the form of an electronic image convertor tube, in which tube the respective collection of primary signal profiles is recorded on a target by means of an electron beam, after which the respective signal profiles are scanned.

14. An apparatus according to claim 2 wherein said first means includes a memory device in the form of a cathode ray tube having a persistent phosphor screen, and that said second means includes an image scanning tube, the collection of primary signal profiles recorded on the screen of said cathode ray tube being displayed by optical means on the entrance window of said image scanning tube.

15. An apparatus according to claim 2 wherein said first means includes a memory device in the form of a continuous two-dimensional magnetic sheet memory, and the first and second means include magnetic heads for the recording of the primary signal profiles and the scanning of the secondary signal profiles.

* * * * *